Figure 1:
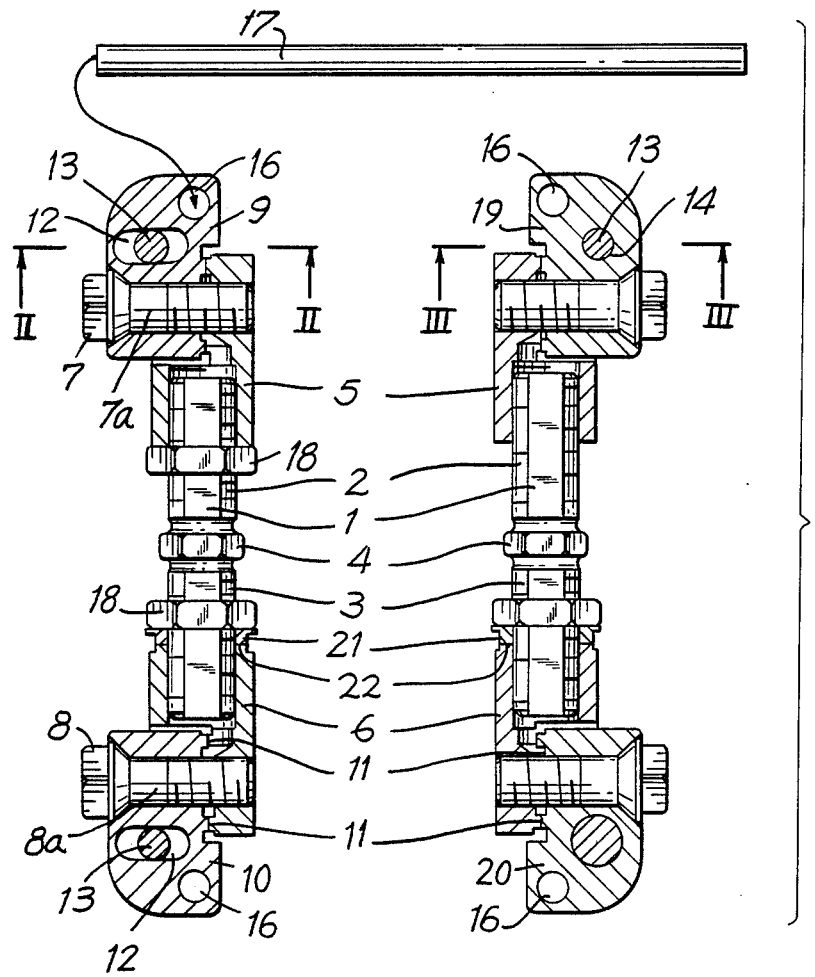

United States Patent [19]

Gotzen et al.

[11] Patent Number: 4,944,743
[45] Date of Patent: Jul. 31, 1990

[54] SPINAL FIXATION DEVICE

[75] Inventors: L. Gotzen, Marburg; Karl-Heinz Kunze, Kiel, both of Fed. Rep. of Germany; Claudius Techow, Oxnard, Calif.

[73] Assignee: Mecron Medizinische Produkte GmbH, Berlin, Fed. Rep. of Germany

[21] Appl. No.: 243,477

[22] Filed: Sep. 12, 1988

[30] Foreign Application Priority Data

Oct. 7, 1987 [DE] Fed. Rep. of Germany ....... 3733924

[51] Int. Cl.⁵ .............................................. A61B 17/58
[52] U.S. Cl. ...................................... 606/61; 606/59; 606/60
[58] Field of Search ........... 128/92 Z, 92 ZZ, 92 ZY, 128/92 ZK, 92 ZW, 92 Y, 92 YM, 92 YJ, 92 YF; 606/60, 61

[56] References Cited

U.S. PATENT DOCUMENTS

| | | | |
|---|---|---|---|
| 2,251,209 | 7/1941 | Stader | 128/92 Z |
| 4,271,832 | 6/1981 | Evans et al. | 128/92 ZW |
| 4,475,546 | 10/1984 | Patton | 128/92 ZZ |
| 4,657,550 | 4/1987 | Daher | 128/92 YM |
| 4,658,809 | 4/1987 | Ulrich | 128/92 YM |
| 4,714,076 | 12/1987 | Compte et al. | 128/92 ZW |
| 4,714,469 | 12/1987 | Kenna | 128/92 YM |
| 4,733,657 | 3/1988 | Kluger | 128/92 ZZ X |

FOREIGN PATENT DOCUMENTS 3132520 6/1982 Fed. Rep. of Germany ........ 128/92 YM

OTHER PUBLICATIONS

Bulletin NR 70, Synthes, 4/1986, Robert Mathys Co.

Primary Examiner—Robert A. Hafer
Assistant Examiner—Kevin G. Rooney
Attorney, Agent, or Firm—John P. White

[57] ABSTRACT

An implantable fixation device comprises a support bar (1) having right-hand threads on the one end and left-hand threads on the opposite end, and having jaw supports (5, 6) threadingly mounted on the respective threaded ends. The jaw supports have secured thereto bolt jaws by means of a respective clamping screw (7), which bolt jaws are (adapted to be) fixed to intact vertebral bodies of the spiral column by means of bone (screw) bolts (13). Further, the bolt jaws are provided with receiving holes (16) permitting the insertion of rod-shaped repositioning instruments (17). By means of this structure, setting of the vertebral elements or segments is possible irrespective of the length of the bone bolts. The repositioning rods (17) can be easily removed; subsequent shortening of the bone bolts (17) is not necessary.

9 Claims, 1 Drawing Sheet

SPINAL FIXATION DEVICE

The present invention relates to a fixation device for a spinal column, for the bridging of at least one defective or affected vertebral segment, comprising a support bar the length of which corresponds to that of the vertebral segment to be bridged, and which has opposite ends thereof provided with threads of opposite hand;

a pair of jaw supports each being threaded, with a corresponding threaded hole, onto one of the two ends of the support bar;

a pair of (screw) bolt jaws, one bolt jaw each being mounted on a jaw support by means of a clamping screw extending perpendicular to the axis of the support bar, with the respective clamping screw defining an axis of rotation, perpendicular or normal to the support bar, for the associated bolt jaw, and the clamping screw, when tightened, locking the bolt jaw relative to the jaw support; and holding means, provided in each bolt jaw, for a (respective) bone (screw) bolt extending approximately perpendicular to the longitudinal axes of the support bar and of the clamping screw.

Devices of this type, usually termed "Fixateur interne", are each implanted in pairs for the setting and supporting of a defective or affected spinal column. In such an instance, normally a maximum of two vertebral segments are bridged, with the bone (screw) bolts, passed through the bolt jaws, being fitted each into a healthy (intact) vertebral body.

A fixation device of the type mentioned above is described in the book by Walter Dick, "Innere Fixation von Brust- und Lendenwirbelfrakturen", pages 56 to 62. This conventional system uses Schanz' (screw) bolts as bone bolts which still have a long shaft projecting beyond the bolt jaws even when they are screwed in place. Using these bolts of excessive length as levers, the vertebral bodies can be set or aligned as long as the clamping screws are not tightened. After the setting step, the bone bolts are locked relative to the bolt jaws by means of the clamping screws, and the bolt jaws are locked relative to the jaw supports. Then, the projecting extensions of the Schanz' bolts must be shortened in a troublesome manner; this may result in complications and even in the intrusion of metal particles into the wound. Further, it is another drawback that the fixing of the Schanz' bolts to the jaws is not independent of the locking of the jaws relative to the support bar. Namely, in this structure the bolt jaws are simple clamping jaws by which the bolt shaft is pressed onto the jaw support when the clamping screws are tightened. This results in drawbacks with respect to stability and handling in the implanting of the fixation device.

Further, DE-OS 34 14 374 shows to be known a device for the setting of a spinal column, wherein extension bars are mounted to the bone bolts fitted into the vertebral body, in order to perform through these extension bars, as levers, the repositioning of the vertebral bodies by means of an external device. In addition, the affected vertebral body then must be mechanically bridged by means of fitted clamping screws or bolts only afterwards, before the extension bars and the external device can be removed. However, it is not disclosed in detail in said literature how the connection between the subsequently fitted clamping screws and the bone bolts is to be established, in order to achieve the desired stability.

It is the object of the present invention to provide a fixation device of the type as outlined above, which permits proper repositioning of the vertebral elements after the fitting of the bone bolts, without requiring subsequent shortening of the bolts in the patient. Furthermore, good and stable guiding or holding of the bone bolts is to be achieved.

According to the present invention, this object is solved in that the preshaped head ends of the bone bolts are each positioned adjacent to the respective bolt jaw when the bone bolts are screwed in place in a vertebral body; and that the bolt jaws are each provided with receiving elements for the releasable engagement of lever-like repositioning instruments.

Thus, in the fixation device according to the invention, the bone bolts have their lengths adjusted from the outset so that after their screwing in place, their heads do not substantially project beyond the bolt jaws in which the bone bolts are guided or held. In order to nevertheless provide for good repositioning of the vertebral bodies, these bolt jaws include engagement facilities for the engagement of a corresponding lever instrument, i.e. in the most basic instance a bored hole for receiving rod-shaped or bar-shaped repositioning instruments.

Expediently, the bone bolts proper are guided in bored holes or openings of the bolt jaws, such that their guiding and connection with the bolt jaws is independent of the tightening of the clamping srews. Depending on demand, the holes, as smooth or backlash-free guide means, may receive the bone bolts, or may allow pivoting of these bone bolts in a plane perpendicular to the axis of the support bar. In this way, the fixation device may be conformed to the respective anatomical situation, while nevertheless providing the desired stability.

Further advantageous embodiments of the invention are disclosed in the subclaims.

Figure 2:
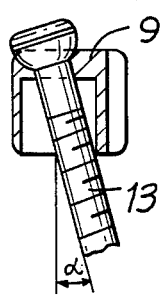
Figure 3:
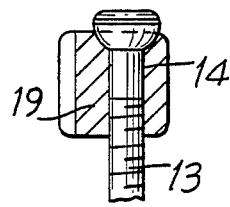
Figure 4:
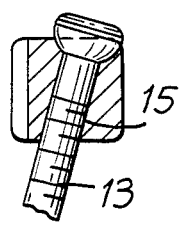

Below, the present invention is explained in embodiments with reference to the drawing, wherein:

FIG. 1 illustrates the positioning of a pair of fixation devices of the type as used with a spinal column, in combination with a rod-shaped repositioning instrument; and FIGS. 2 to 4 each are detailed views in section along lines II—II and III—III in FIG. 1, respectively.

FIG. 1 illustrates a pair of fixation devices of identical basic structure, which are arranged in a symmetrical relation in accordance with their respective use; here, a few alternative modifications are shown in the left or the right device only. Normally, the two devices are implanted in the spinal column on either side of the spinal processes in the illustrated position in a symmetrical (mirror image-like) fashion, whereby a defective vertebral element or segment is bridged and the ends of the pair of fixation devices are each threadingly secured to an intact vertebral elements.

Each of the two fixation devices according to FIG. 1 includes a support bar 1 which has both ends thereof provided with threads of opposite hand, i.e. with right-hand threads 2 on the one end and with left-hand threads 3 on the other end. For example, the center portion is formed as a hexagon for the engagement of a wrench; however, other means for the engagement of a rotating tool are also conceivable. Each of the two threaded ends 2 and 3, respectively, of the support bar 1 has threadingly connected therewith a jaw carrier or support 5 or 6, respectively, provided with corresponding threads. By rotating the support bar 1, the two jaw supports are moved toward each other or apart from each other through the right-hand/left-hand threads, whereby the relative distance between these jaw supports can be set.

Each jaw support 5 or 6 has secured thereto a bolt jaw 9 or 10, respectively, by means of a clamping screw 7 or 8, respectively. The clamping screws 7 have their axes extending perpendicular (normal) to the axis of the support bar 1, and they permit rotating of the jaw supports 9 or 10, respectively, about the associated axis 7a or 8a, respectively, unless the clamping screws 7 or 8, respectively, are tightened. When the clamping screws 7 and 8 are tightened, the bolt jaws 9 and 10 are locked on the clamping faces 11 relative to the jaw supports. Such locking is ensured by serrations or corrugations in the clamping faces 11.

Each bolt jaw has receiving means for a bone bolt, with the bolt jaws 9 and 10 shown in the left part of FIG. 1 each having an ovally elongated receiving hole 12; these receiving holes 12 permit pivoting of the bone bolt 13 under a given angle o in a plane extending approximately perpendicular to the support bar 1. This pivoting angle is shown in the sectional view II—II of FIG. 2.

The fixation device shown in the right position in FIG. 1 and including the bolt jaws 19 and 20, is provided with receiving holes 14 which form a smooth or backlash-free guide (socket) for the respective bone bolt 13. This structure is shown in the sectional view of FIG. 3 wherein the bone bolt 13 extends perpendicular to the axis of the support bar 1 and perpendicular to the axis of the clamping screw 7. FIG. 4 illustrates a modification with respect to FIG. 3. Here, a receiving hole 15 is shown in which the bone bolt 13 is held without play, but at a given angle.

Still further, the bolt jaws 9 and 10 or 19 and 20, respectively, are each provided with a (bored) hole 16 which extends substantially in parallel with the bone bolt 13. Upon screwing the bone bolts 13 in position in the respective intact (healthy) vertebral body, then a repositioning instrument, e.g. the rod 17 shown in FIG. 1, may be fitted into the respective hole 16, in order to rotate by means of this rod, as a lever, the corresponding bolt jaw in such a way that the vertebral body joined therewith is set in the desired manner. Following this repositioning step, the clamping screws 7 and 8 are tightened, whereby the vertebral bodies are fixed in their relative position. The rods 17 can be easily removed from the holes 16 such that protruding or projecting parts are no longer present on the implantate. In this way, bone bolts 13 with heads may be used which fully or at least substantially fully disappear within the bolt jaws to be flush with the surface of the latter. Accordingly, it is absolutely unnecessary to shorten the bone bolts subsequently.

Expediently, the distance set between the pair of jaw supports 5 and 6 on the support bar 1 is fixed by means of counter or lock nuts 18. Additionally, between the respective lock nut 18 and the jaw support 5 or 6, respectively, a washer 21 may be provided which is slidably mounted on the support bar while being fixed against rotation, which washer provides for extra locking because of embossed serrations 22 in the end face thereof.

We claim:
1. An implantable spinal column vertebral fixation for bridging at least one vertebral segment, comprising:
   (a) a support bar having a longitudinal axis with a length corresponding to the vertebral segment which is to be bridged and having ends thereof threaded in opposite rotational directions;
   (b) a pair of threaded jaw supports which are attachable to the two threaded support bar ends;
   (c) a plurality of bone screws having heads extending radially from one end of the screw;
   (d) a pair of bolt jaws rotatively attachable to the jaw supports and defining an axis of rotation between the jaws and the jaw support which is perpendicular to the support bar longitudinal axis, the bolt jaws each having a clamping screw oriented perpendicularly to the support bar longitudinal axis with the clamping screw selectively attachable to the jaw supports for rigidly locking the jaw support to the bolt jaw, the clamping screw having a longitudinal axis;
   (e) means for receiving the bone screws within the bolt jaw, which are oriented for captured passage of the bone screw therethrough in a direction generally perpendicular to each of the support bar and clamping screw longitudinal axes, so that the bone screws can be tightened with the heads substantially flush with the bolt jaw without cutting the bone screws; and
   (f) the bolt jaws having recesses directly therein separate from the receiving means for engagement of lever-like positioning instruments, for alignment of vertebral segments attached to the fixation device.

2. The fixation device of claim 1, wherein the means for receiving bone screws is a bored hole having a diameter selected to receive the bone screw in backlash-free fashion without the need for a tensioning device between the bored hole and the screw.

3. The fixation device of claim 2, wherein the bored hole is oriented at a selected angle within a plane extending generally perpendicularly to the support bar longitudinal axis.

4. The fixation device of claim 1, wherein the means for receiving bone screws is a recess in the bolt jaw which is configured to permit pivoting of the bone screw within an angular range within a plane extending generally perpendicularly to the support bar longitudinal axis.

5. The fixation device of any one of claims 1 to 4, wherein the engagement recesses are bored holes for insertion of rod-shaped positioning instruments.

6. The fixation device of claim 5, wherein the engagement recess bored holes are substantially parallel with the bone screws.

7. The fixation device of any one of claims 1 to 4 wherein the jaw supports and bolt jaws have abutting faces having locking serrations.

8. The fixation device of claim 1, wherein the support bar has a lock nut on each end thereof for locking the jaw supports thereto.

9. The fixation device of claim 8 wherein the support bar has lockwashers having serrated contact faces interposed between the jaw supports and the lock nuts.

* * * * *